US00PP13567P2

(12) United States Plant Patent
Kolster

(10) Patent No.: US PP13,567 P2
(45) Date of Patent: Feb. 18, 2003

(54) WEIGELA PLANT NAMED 'KOLSUNN'

(75) Inventor: Peter R. Kolster, Boskoop (NL)

(73) Assignee: Gebr. Kolster B.V., Boskoop (NL)

( * ) Notice: Subject to any disclaimer, the term of this patent is extended or adjusted under 35 U.S.C. 154(b) by 0 days.

(21) Appl. No.: 10/006,830

(22) Filed: Dec. 5, 2001

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database, 2002/03, GTI Jouve Retrieval Software, citation for 'Kolsunn'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Weigela plant named 'Kolsunn', characterized by its upright and outwardly spreading plant habit; dark reddish brown young stem coloration; and green and white variegated leaves.

2 Drawing Sheets

BOTANICAL CLASSIFICATION/CULTIVAR DESIGNATION

*Weigela florida* cultivar Kolsunn.

BACKGROUND OF THE INVENTION

The present Invention relates to a new and distinct cultivar of Weigela plant, botanically known as *Weigela florida*, and hereinafter referred to by the name 'Kolsunn'.

The new cultivar is a naturally-occurring whole plant mutation of the *Weigela florida* 'Variegata', not patented. The new Weigela was discovered by the Inventor in 1996 in a controlled environment in Amstelveen, The Netherlands, within a population of plants of 'Variegata'. The cultivar Kolsunn was discovered and selected by the Inventor on the basis of its green and white variegated leaves.

Asexual reproduction of the new Weigela by terminal cuttings taken at Boskoop, The Netherlands, has shown that the unique features of this new Weigela are stable and reproduced true to type in successive generations of asexual reproduction.

SUMMARY OF THE INVENTION

The following traits have been repeatedly observed and are determined to be the unique characteristics of 'Kolsunn'. These characteristics in combination distinguish 'Kolsunn' as a new and distinct cultivar:

1. Upright and outwardly spreading plant habit.
2. Dark reddish brown young stem coloration.
3. Green and white variegated leaves.

Plants of the new Weigela are most similar to plants of the parent, the Weigela 'Variegata'. However, plants of the new Weigela differ from plants of 'Variegata' in leaf coloration as leaves of plants of 'Variegata' are green and yellow in color.

BRIEF DESCRIPTION OF THE PHOTOGRAPHS

The accompanying colored photographs illustrate the overall appearance of the new Weigela, showing the colors as true as it is reasonably possible to obtain in colored reproductions of this type. Colors in the photographs may differ slightly from the color values cited in the detailed botanical description which accurately describe the colors of the new Weigela.

The photograph on the first sheet comprises a side perspective view of a typical plant of 'Kolsunn'.

The photograph at the top of the second sheet is a close-up view of a typical lateral branch of 'Kolsunn'.

The photograph at the middle of the second sheet is a close-up view of typical upper surfaces of fully expanded and developing leaves of 'Kolsunn'.

The photograph at the bottom of the second sheet comprises a close-up view of the upper surface of a typical flower of 'Kolsunn'.

DETAILED BOTANICAL DESCRIPTION

The new Weigela has not been observed under all possible environmental conditions. The phenotype may vary somewhat with variations in environment such as temperature and light intensity, without, however, any variance in genotype.

The aforementioned photographs, following observations and measurements describe plants grown in Boskoop, The Netherlands, in an outdoor nursery and under commercial production practices. Plants were about two years old and pruned annually. The photographs and description were taken during the late summer when day temperatures ranged from 14 to 20° C. and night temperatures ranged from 7 to 12° C.

In the following description, color references are made to The Royal Horticultural Society Colour Chart, 2001 Edition, except where general terms of ordinary dictionary significance are used.

Botanical classification: *Weigela florida* cultivar Kolsunn.
Parentage: Naturally-occurring whole plant mutation of *Weigela florida* 'Variegata', not patented.
Propagation:
- *Type.*—Terminal cuttings.
- *Time to initiate roots.*—Summer: About 30 days at 20° C. Winter: About 50 days at 12° C.
- *Time to produce a rooted young plant.*—Summer: About 90 days at 20° C. Winter: About 120 days at 12° C.

*Root description.*—Freely branching; medium thickness; brown in color.

Plant description:

*Plant form.*—Upright and outwardly spreading perennial shrub.

*Growth habit.*—Vigorous; dense and bushy growth habit.

*Plant height.*—About 2 m.

*Plant width* (*spread*).—About 2 m.

*Growth rate.*—Plants grow about 25 cm per month during the spring in Boskoop, The Netherlands.

*Lateral branches.*—Length: About 30 cm. Diameter: About 3 mm. Internode length: About 5.5 cm. Strength: Strong. Texture: Glabrous. Color: Young: 176A to 178A. Woody: N199B to N199C. Lenticels: Density: Sparse. Length: About 1.5 mm. Width: About 0.5 mm. Color: On young stems: Close to 198C. On woody stems: 198D.

*Foliage description.*—Leaves opposite, single, and generally symmetrical. Length: About 10 cm. Width: About 4.9 cm. Shape: Ovate to elliptic. Apex: Apiculate. Base: Attenuate. Margin: Finely serrulate. Texture, upper and lower surfaces: Slightly rugose; very short hairs mostly along veins. Venation pattern: Pinnate. Color: Developing leaves, upper surface: Central area, between 146A and 137A; surrounded by 158A; at edge of margin, 58A. Developing leaves, lower surface: Central area, 138B; surrounded by 159B tinted with 63D; at edge of margin, 58A. Fully expanded leaves, upper surface: Central area, between 147A and 137A; surrounded by 158C to 158D. Fully expanded leaves, lower surface: Central area, 138B and 191A; surrounded by 160C to 160D. Vein color, upper surface: 194A. Vein color, lower surface: 194A; towards base, 165B. Petiole: Length: About 5 mm. Diameter: About 2 mm. Color: Upper surface: 146C. Lower surface: 165B.

Flower description:

*Flower type and habit.*—Pink single campanulate flowers arranged in terminal and axillary pairs or small clusters of three to four flowers; about 58 flowers and flower buds per lateral branch. Flowers not persistent. Flowers face mostly upright or slightly outward.

*Natural flowering season.*—Plants flower twice a year. First flowering period is in the spring, typically May in Boskoop, The Netherlands; the second flowering period is late summer, typically late August to early September in Boskoop, The Netherlands; flowering periods last about one month; flowering continuous during these periods.

*Postproduction longevity.*—Flowers typically last about five days on the plant.

*Fragrance.*—Very faint, sweet and slightly lemon-like.

*Flower buds.*—Height: About 3 cm. Diameter: About 1 cm. Shape: Oblanceolate. Color: Mostly 63B; towards the apex, 62D; towards the base, 157D.

*Flowers.*—Diameter: About 2.6 cm. Depth: About 3.5 cm.

*Petals.*—Quantity per flower: Five, fused at base. Length: About 3.9 cm. Width: About 1 cm. Shape: Oblanceolate. Aspect: Apices, slightly reflexed. Apex: Obtuse. Margin: Entire. Texture, upper and lower surfaces: Smooth. Color: When opening, upper surface: 65B to 65C. When opening, lower surface: 64C to 64D. Fully opened, upper surface: 64D to 65A. Fully opened, lower surface: 64D.

*Sepals.*—Quantity per flower: Five, fused at base. Length: About 9 mm. Width: About 1.5 mm. Shape: Narrowly lanceolate to linear. Apex: Acute. Margin: Entire. Texture: Upper surface: Smooth; glabrous. Lower surface: Pubescent. Color: Developing and fully expanded sepals, upper surface: 144A. Developing and fully expanded sepals, lower surface: 144A to 144B.

*Peduncles.*—Length: About 1 cm. Diameter: About 1 mm. Orientation: About 5 to 25° from vertical. Strength: Moderately strong. Color: 143B.

*Reproductive organs.*—Stamens: Quantity per flower: About five. Anther shape: Narrowly oblong. Anther length: About 4.5 mm. Anther color: 165B to 165C. Pollen amount: Scarce. Pollen color: 155A. Pistils: Quantity per flower: One. Pistil length: About 3.4 mm. Stigma shape: Globular, flattened. Stigma color: 155A. Style length: About 3.3 mm. Style color: 155A. Ovary color: 154C.

*Fruits.*—Quantity per flower: One. Days to ripening: About 150. Type: Capsule. Shape: Oblong. Length: About 1.8 cm. Diameter: About 2.5 mm. Texture: Smooth, glabrous. Color: 200B.

*Seeds.*—Quantity per fruit: More than 100. Length: Less than 0.5 mm. Diameter: Less than 0.5 mm. Color: Light brown.

Disease/pest resistance: Plants of the new Weigela have not been observed to be resistant to pathogens and pests common to Weigela.

Temperature tolerance: Plants of the new Weigela have been observed to tolerate temperatures ranging from −30 to 35° C.

It is claimed:

1. A new and distinct cultivar of Weigela plant named 'Kolsunn', as illustrated and described.

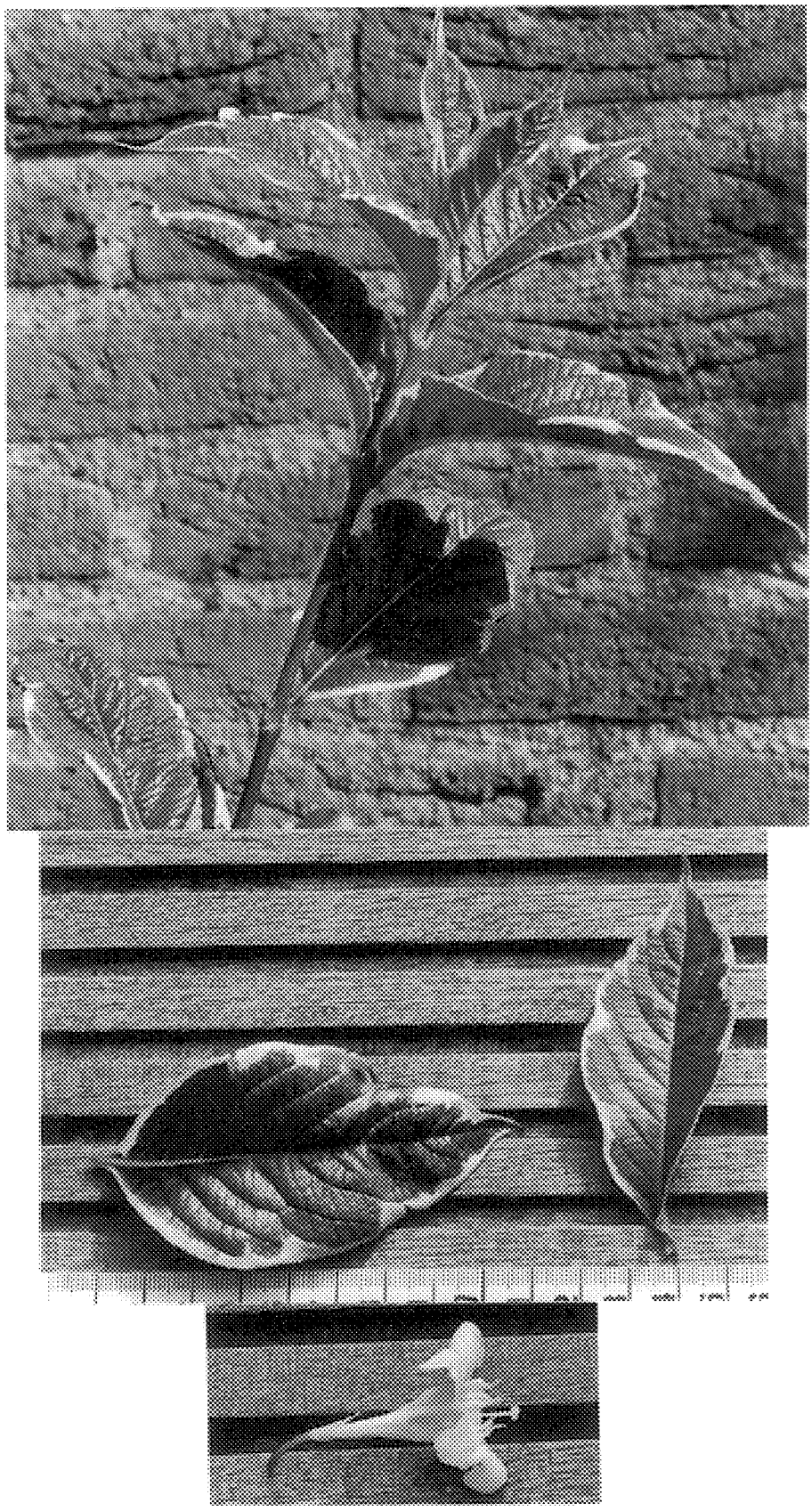

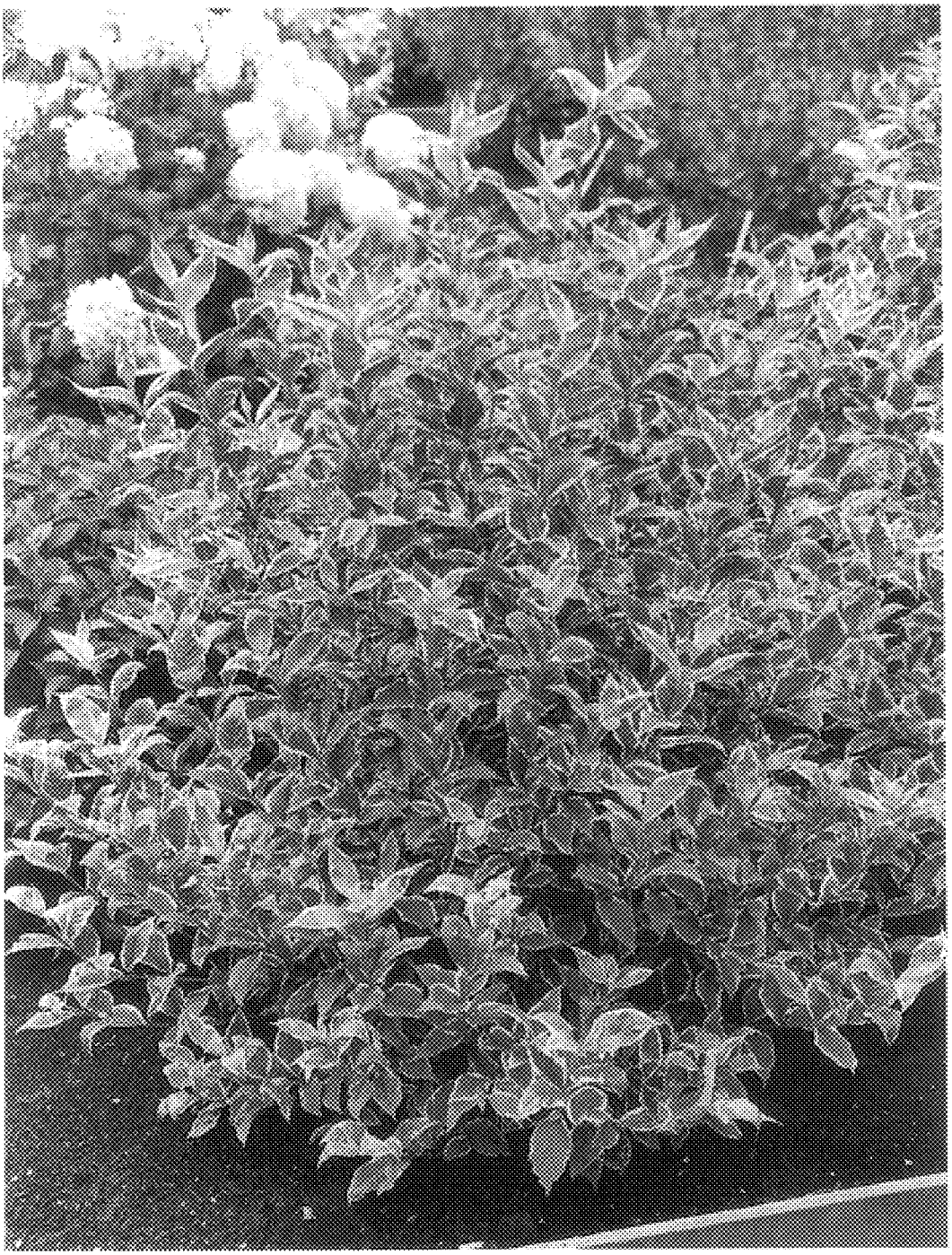

* * * * *